United States Patent
Torstensson et al.

(10) Patent No.: US 6,503,238 B1
(45) Date of Patent: Jan. 7, 2003

(54) DISPOSABLE LIQUID ABSORBENT ARTICLE WITH ELASTICIZING MEMBERS

(75) Inventors: Ingela Torstensson, Mölnlycke; Peter Rönnberg, Mölndal; Olle Carlbark, Kållered; Lennart Nilsson, Skärhamn; Johan Skogsberg, Göteborg, all of (SE)

(73) Assignee: SCA Hygiene Products AB, Gothenburg (SE)

( * ) Notice: Subject to any disclaimer, the term of this patent is extended or adjusted under 35 U.S.C. 154(b) by 710 days.

(21) Appl. No.: 09/594,500

(22) Filed: Jun. 16, 2000

(51) Int. Cl.⁷ .................................. A61F 13/15
(52) U.S. Cl. .................................. 604/385.28
(58) Field of Search ................. 604/385, 28, 385.101, 604/385.21, 385.01

(56) References Cited

U.S. PATENT DOCUMENTS

| | | |
|---|---|---|
| 3,860,003 A | 1/1975 | Buell |
| 4,050,462 A | 9/1977 | Woon et al. |
| 4,281,619 A | 8/1981 | Frick et al. |
| 4,501,587 A | 2/1985 | Enloe |
| 4,585,448 A | 4/1986 | Enloe |
| 4,666,647 A | 5/1987 | Enloe et al. |
| 4,685,916 A | 8/1987 | Enloe |
| 4,704,116 A | 11/1987 | Enloe |
| 4,743,246 A | 5/1988 | Lawson |
| 4,753,646 A | 6/1988 | Enloe |
| 4,761,258 A | 8/1988 | Enloe |
| 4,762,521 A | 8/1988 | Roessler et al. |
| 4,795,454 A | 1/1989 | Dragoo |
| 4,801,345 A | 1/1989 | Dussaud et al. |
| 4,846,823 A | 7/1989 | Enloe |
| 4,846,825 A | 7/1989 | Enloe et al. |
| 4,850,990 A | 7/1989 | Huntoon et al. |
| 4,861,652 A | 8/1989 | Lippert et al. |
| 4,895,568 A | 1/1990 | Enloe |
| 4,900,384 A * | 2/1990 | Sanders et al. |
| 4,916,005 A | 4/1990 | Lippert et al. |
| 5,246,431 A * | 9/1993 | Minetola et al. |
| 5,403,301 A * | 4/1995 | Huffman et al. |
| 5,413,570 A | 5/1995 | Enloe |
| 5,415,644 A | 5/1995 | Enloe |
| 5,582,606 A * | 12/1996 | Bruemmer et al. |
| 5,599,338 A | 2/1997 | Enloe |
| 5,624,425 A * | 4/1997 | Gray et al. |
| 5,643,243 A | 7/1997 | Klemp |
| 5,665,191 A | 9/1997 | Johansson et al. |
| 5,741,241 A | 4/1998 | Guidotti et al. |
| 5,752,946 A | 5/1998 | Boberg et al. |
| 5,876,390 A | 3/1999 | Hall et al. |
| 5,885,266 A | 3/1999 | Chihani et al. |
| 5,928,211 A | 7/1999 | Gustafsson et al. |
| 5,935,682 A | 8/1999 | Wallström |
| 5,985,065 A | 11/1999 | Kling |
| 5,989,370 A | 11/1999 | Wannebo |
| 5,990,375 A | 11/1999 | Lindquist et al. |

FOREIGN PATENT DOCUMENTS

| | | |
|---|---|---|
| EP | 0 219 316 A2 | 4/1987 |
| GB | 2 156 681 A | 10/1985 |
| GB | 2 168 253 A | 6/1986 |
| GB | 2 234 157 A | 1/1991 |
| WO | 88/00010 | 1/1988 |
| WO | 88/04547 | 6/1988 |

* cited by examiner

Primary Examiner—Dennis Ruhl
(74) Attorney, Agent, or Firm—Burns, Doane, Swecker & Mathis, L.L.P.

(57) ABSTRACT

An absorbent article suitable for use as a diaper or adult incontinence garment includes an absorbent body disposed between a cover sheet, an inner sheet. Longitudinally extending folds disposed on the inner sheet inhibit the leakage of bodily exudates from the edges of the article. Elastic members extend along a portion of the length of the folds in the mid portion of the article. In the back portion of the article, elastic members connected to the inner sheet extend adjacent the edges of the absorbent body to enhance the fit of the garment. In the front portion of the article, elastic members may also be connected to the inner sheet and extend adjacent the edges of the absorbent body to enhance the fit of the garment.

35 Claims, 6 Drawing Sheets

DISPOSABLE LIQUID ABSORBENT ARTICLE WITH ELASTICIZING MEMBERS

BACKGROUND

1. Field of the Invention

The present invention relates to a disposable liquid absorbent article with elasticizing members.

2. Discussion of Related Art

Liquid-absorbent articles, for example incontinence garments such as diapers, may be provided with elastics in order to provide a desired shape when the diaper is positioned on the body of a user. In many articles of this kind the main purpose of the elastics is to provide, at the wearer's crotch, a raised edge or cuff, sealing against the wearer's legs.

For example, U.S. Pat. No. 3,860,003, describes a diaper in which leg elastics provide a circumferential cuff around the legs. When the diaper is spread flat, the elastics are fully rectilinear and substantially extending along the side of the absorption body in order to make the edge of the diaper seal against the legs in an in-use position.

U.S. Pat. No. 4,050,462 describes a diaper in which the elastics extend rectilinearly when the diaper is spread flat and which contract the crotch section of the diaper and, by folding, increase the surface and the volume per length unit for the absorption body in order to achieve an enhanced absorption effect.

WO 88/00010 describes a diaper having substantially rectilinear elastics, forming a V-shaped configuration. The elastics extend over the absorption body of the diaper and delimit an area that is altered in shape by the contracting effect of the elastics. By the extension of the elastics with rectilinear sections, a folding of the article as a whole is substantially achieved as a result of the tendency of the elastics to reduce the entire length of the article.

U.S. Pat. No. 4,801,345 describes a method for manufacturing diapers. The method includes the application of elastics along the crotch section of the diapers. The elastics hereby extend concavely outward along the longitudinal edges of the diaper and completely to the side of the absorption body. The primary purpose of the elastics is to provide a seal between the edge of the diaper and the wearer's legs. A further effect will be a certain contraction and folding of the absorption body over the crotch section.

EP 0 219 326 describes a diaper with elastics extending completely rectilinearly in when the diaper is flat and completely to the side of the absorption body. Elastics are arranged partly at the outer edge of the diaper on each side of the crotch section and partly in an edge-band on each side of the absorption body. In addition to maintaining an upstanding, sealing edge by way of the edge-band, the elastics ensure a certain folding and contraction of the absorption body.

GB 2 234 157 describes a diaper with elastics extending around the waistline, along the edge of the crotch section against the wearer's legs, and also across the crotch section. The elastics for sealing around the legs reduce the risk of leakage, while the elastics across the crotch section are arranged to enable a rational application of continuous elastic cord. The composition and method is specially adapted to trouser-shaped diapers.

U.S. Pat. Nos. 4,704,116; 4,846,823; 5,415,644; and 5,559,338 to Enloe describe a diaper including elasticized leg gatherers and first and second elasticized fluid pervious flaps spaced inwardly from the leg gatherers and defining a waste containment pocket. Solid fecal material collects and is contained in the pockets, while fluidic fecal material is collected by the pockets and is essentially strained, allowing the liquid portion to be absorbed by the absorbent pad or body of the garment.

A problem with diapers of the type disclosed by Enloe is that the double flaps (the first and second flaps) constitute additional bulk and possible rough edges that can create skin irritations on the user.

OBJECTS AND SUMMARY

An absorbent article in accordance with the present invention is adapted to provide protection against leakage of bodily exudates and, when in use, to assume a shape that conforms to a user's body, thereby reducing the conspicuousness of the article when worn by a user. In addition, an absorbent article in accordance with the present invention is constructed to provide for efficient use of materials and manufacturing resources.

In brief summary, an absorbent article in accordance with the present invention includes a disposable, liquid absorbent article having a front portion, a rear portion, and a mid portion between the front portion and the rear portion. The article comprises a liquid impervious cover sheet; an inner sheet connected to the cover sheet; and an absorbent body disposed between the inner sheet and the cover sheet and having a major axis extending substantially along a longitudinal axis of the article. The article further includes a first standing gather extending from the inner sheet on a first side of the longitudinal axis substantially along an axis parallel to the longitudinal axis, the first standing gather extending from at least the front portion and the mid portion of the absorbent article, the first standing gather having elastication extending only from a first longitudinal position to a second longitudinal position, wherein the first longitudinal position is at or near the front portion and the second longitudinal position is at or near the mid portion; and a second standing gather extending from the inner sheet on a second side of the longitudinal axis substantially along an axis parallel to the longitudinal axis, the second standing gather extending from at least the front portion and the mid portion of the absorbent article, the second standing gather having elastication extending only from the first longitudinal position to the second longitudinal position. The article also includes a first elasticizing means arranged between the inner sheet and the outer sheet on a first side of the longitudinal axis and extending along an outer edge of the absorbent article from only about the second longitudinal position to a third longitudinal position, wherein the third longitudinal position is at or near the rear portion so as to gather a portion of the inner and outer sheet; and a second elasticizing means arranged between the inner sheet and the outer sheet on a second side of the longitudinal axis and extending along an outer edge of the absorbent article from only about the second longitudinal position to the third longitudinal position In another embodiment, the invention provides a disposable, liquid absorbent article. The article comprises a liquid impervious cover sheet, an inner sheet connected to the cover sheet, an absorbent body disposed between the inner sheet and the cover sheet and having a major axis extending substantially along a longitudinal axis of the article, first and second folds having a length extending substantially along an axis parallel to the longitudinal axis, and elasticizing means extending along portions of the first and second folds in at least the crotch portion of the article, and extending therefrom toward the rear portion of the article, following a contour adjacent the edge of the absorbent body.

In another embodiment, the invention provides a disposable, liquid absorbent article. The article comprises a liquid impervious cover sheet, an inner sheet connected to the cover sheet, an absorbent body disposed between the inner sheet and the cover sheet and having a major axis extending substantially along a longitudinal axis of the article, first and second folds having a length extending substantially along an axis parallel to the longitudinal axis, and having elasticizing means extending along portions of the first and second folds from a position proximate the front portion of the article to a position proximate a crotch portion of the article, and elasticizing means extending from the crotch portion of article toward the rear portion of the article, following a contour adjacent the edge of the absorbent body.

BRIEF DESCRIPTION OF THE DRAWINGS

These and other objects, features and advantages of the present invention will become more readily apparent to those skilled in the art upon reading the following detailed description, in conjunction with the appended drawings, in which.

DETAILED DESCRIPTION OF THE PREFERRED EMBODIMENTS

Figure 1:
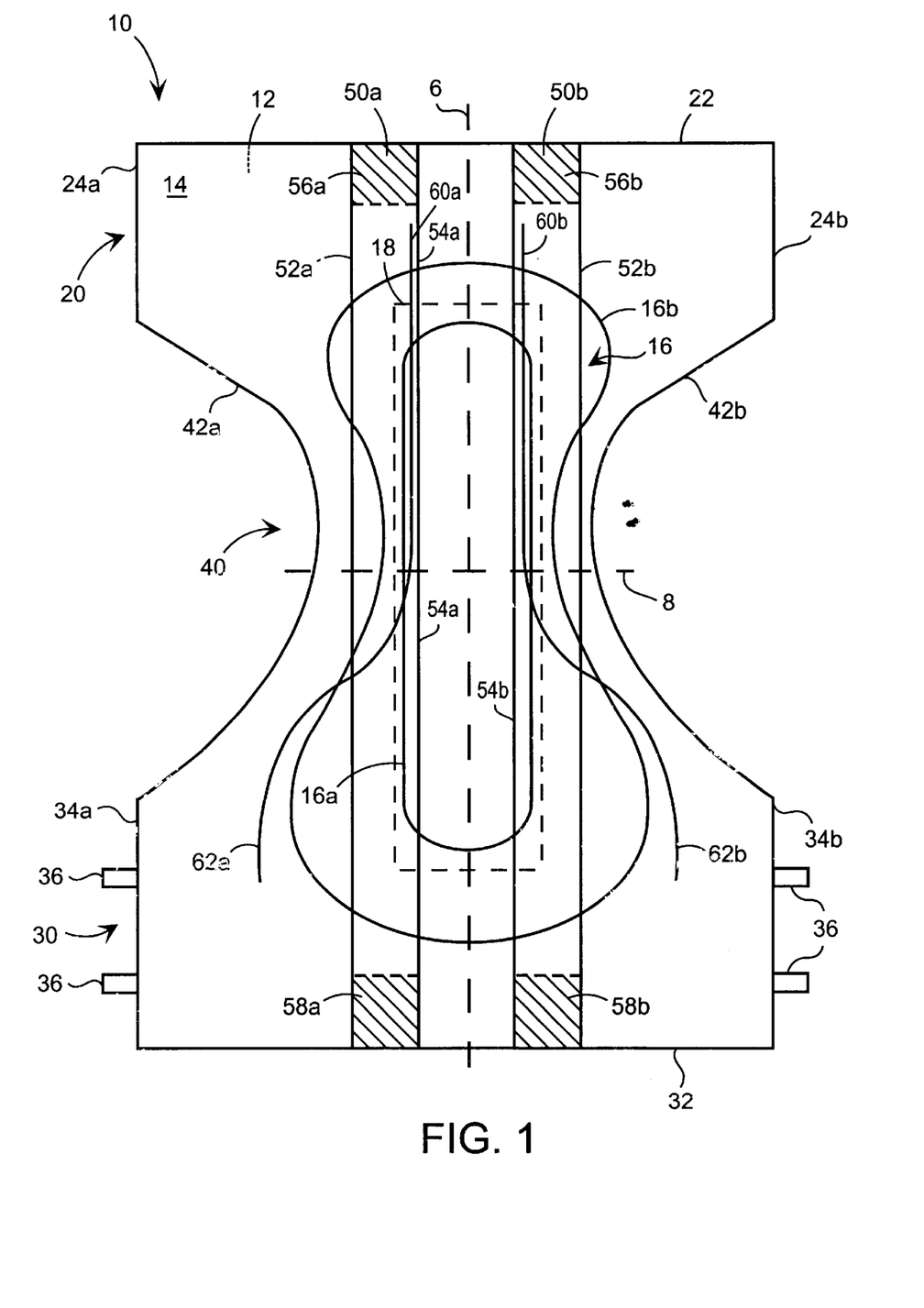
FIG. 1 is a plan view of an absorbent article in accordance with a first exemplary embodiment of the present invention.
Figure 2:
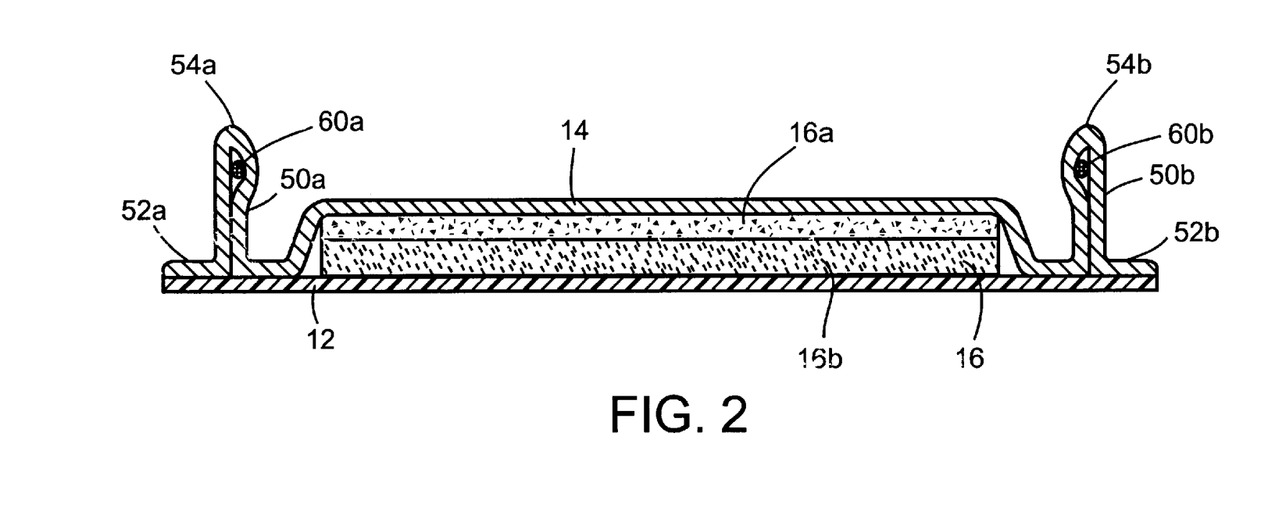
FIG. 2 is a cross-sectional view of the absorbent article depicted in FIG. 1 taken along line 8.

An absorbent article 10 in accordance with the invention includes an inner sheet 14 intended to be positioned in contact with the body of a user, an absorbent body 16 for receiving and retaining bodily exudates (e.g., urine and fecal matter), and a cover sheet 12. A first fold 50a and a second fold 50b extend along the surface of inner sheet 14 parallel to a longitudinal axis 6 of the absorbent article 10. Folds 50a, 50b include respective elastic strips 60a, 60b extending along a portion of their length.

The cover sheet 12 may include a suitable material which typically is a substantially liquid impermeable material. Commonly used materials include a thin (e.g., 20 μ) layer of polyethylene, polypropylene, polyvinyl-chloride, or other suitable material. The cover sheet 12 may be constructed of a single-layer or of multiple layers.

The absorbent body 16 may include materials suitable for absorbing bodily exudates. Known materials include cellulosic fibers, tissue, or super-absorbent materials, which are polymers capable of absorbing several times their own weight in liquids. The invention contemplates the use of multi-layered and/or composite absorbent bodies, which, by way of example, are described in U.S. Pat. No. 5,741,241 assigned to SCA Molnlycke AB, Gothenburg, Sweden, the disclosure of which is incorporated by reference herein in its entirety. For example, the absorbent body 16 may include a first absorbent layer 16a that includes a cellulose fluff-pulp of large pore volume, high wet resiliency and low liquid-dispersion ability, and a second absorbent layer 16b comprised of cellulose fluff-pulp of low pore volume, low wet resiliency and high liquid-dispersion ability. Both absorbent layers may also include superabsorbent material. Or, either of the layers may include superabsorbent material.

The inner sheet 14 is attached to the inner surface of the cover sheet 12 with the absorbent body 16 secured between the cover sheet 12 and the inner sheet 14. The inner sheet 14 may be secured to the cover sheet 12 using conventional techniques, e.g., ultrasonic welding, adhesives, etc.

In a preferred embodiment, the inner sheet 14 is preferably a nonwoven material that is produced in a liquid impermeable condition so that it is substantially liquid impermeable under normal use conditions. The nonwoven material can be either hydrophilic or hydrophobic. The material is preferably an SMS material (spunbond-meltbond-spunbond). The permeability of the inner sheet is measured in mm of water according to a test called the Edana method No. 120.1-80.

A specific region of the inner sheet 14, referred to as a wetting area 18, may be treated, e.g., by exposure to a hydrophilic surfactant, to make the wetting area 18 liquid permeable. As such, the wetting area 18 preferably has a permeability of 0 mm $H_2O$, and the portions of the inner sheet forming the folds 50a, 50b preferably have a permeability of at least 20 mm $H_2O$.

Alternately, the inner sheet 14 may be formed from a liquid permeable material.

Details of the construction of the absorbent article 10 will be described more particularly with reference to FIGS. 1 and 2. FIG. 1 is a plan view of an exemplary embodiment of an absorbent article disposed in a substantially flat position. When laid flat, the absorbent article 10 has a substantially hour-glass contour and has a length extending along a major or longitudinal axis 6 and a width extending along a minor axis 8 perpendicular to longitudinal axis 6. A first longitudinal end constitutes a front portion 20 (also referred to as a front region), and the other end constitutes a rear portion 30 (also referred to as a rear region). A mid portion 40 (also referred to as a mid region) is located between the front portion 20 and the rear portion 30.

The front portion 20 includes a front edge 22 and side edges 24a and 24b. In the embodiment illustrated in FIG. 1, the front edge 22 is substantially straight; however, it will be appreciated that the front edge 22 may be contoured or curved to adapt to a desired shape in use. Similarly, the side edges 24a, 24b are depicted as substantially straight, but may be contoured or curved as desired.

The rear portion 30 includes a rear edge 32 and side edges 34a, 34b, which are depicted as straight but may be contoured or curved as desired. The rear portion 30 further includes fasteners 36. Tapes, hook and loop material, pins, and other conventional fasteners are all known fasteners in the incontinence garment art, and are only some of the types of fasteners which may be used with this embodiment. In use, the side edge 24a is fastened to the side edge 34a and the side edge 24b is fastened to the side edge 34b to define a waist portion of a disposable absorbent garment.

The mid portion 40 includes contoured edges 42a, 42b. In use, the contoured edges 42a, 42b are adapted to be disposed adjacent the legs of the wearer of the absorbent article 10 proximate the crotch area, and the mid portion 40 is positioned to receive and retain bodily exudates.

The inner sheet 14 may be applied to the cover sheet 12 such that a first fold 50a and a second fold 50b are incorporated therein along the longitudinal length of the article at a location proximate each edge of the narrowest part of the absorbent body 16. This may be accomplished, for example, by forming the folds 50a, 50b in the inner sheet 14 before or while connecting inner sheet 14 to cover sheet 12. The folds 50a, 50b include proximal edges 52a and 52b in contact with the inner sheet 14 and distal edges 54a and 54b opposite the proximal edges 52a, 52b.

In the embodiment depicted in FIGS. 1–2, the folds 50a, 50b extend from the front edge 22 to the rear edge 32 along axes substantially parallel to the longitudinal axis 6. It will be appreciated, however, that the folds 50a, 50b may follow a convex or concave arc from front the front section 20 to the rear section 30 of the absorbent article 10. The entire width of the fold 50a may be connected to the surface of the garment at a front portion 56a and at a rear portion 58a. Similarly, the entire width of the fold 50b may be connected to the surface of the garment at a front portion 56b and at a rear portion 58b. In the embodiment of the invention which utilizes a liquid impermeable inner sheet 14, the folds of the inner sheet 14 are made from the liquid impermeable portion of the inner sheet 14, such that the folds are substantially liquid impermeable.

As an alternative to applying the inner sheet 14 with the folds described in the preceding paragraph and illustrated in FIGS. 1 and 2, a substantially flat inner sheet 14 may be used, i.e., without the folds. In this case, separate sheets of material may be applied to the surface of the inner sheet 14 to form the folds. See, for example, the embodiments illustrated in FIGS. 5–8.

An absorbent article in accordance with the present invention includes elastic members to inhibit leakage of bodily exudates. More particularly, in one embodiment at least one elastic member 60a extends along a portion of the length of the fold 50a, preferably from a location proximate the front edge 22 of the absorbent article 10 to a location in the mid portion 40 of the absorbent article 10. Similarly, at least one elastic member 60b extends along a portion of the length of the fold 50b, preferably from a location proximate the front edge 22 of the absorbent article 10 to a location in the mid portion 40 of the absorbent article 10. The elastic members 60a, 60b are preferably applied to the absorbent article 10 under tension, so that when the article is unfolded (e.g., when it is in use), tension in the elastic members 60a, 60b gathers the distal edges 54a, 54b of the folds 50a, 50b and urges the distal edges 54a, 54b away from the surface of the inner sheet 14. The folds 50a, 50b thereby form barriers to inhibit the leakage of bodily exudates from the mid region 40 of the absorbent article 10. In the areas where the elastics gather the folds and urge the folds away from the surface of the inner sheet, the folds may be referred to as standing gathers.

The absorbent article 10 also utilizes elastic members to facilitate shaping the article in a manner to reduce its conspicuousness and increase its comfort when in use, particularly desirable features when the article is used as an adult incontinence garment. At least one elastic member 62a extends from a position in the mid portion 40 of the article 10 to a position in the rear portion 30 of the article 10, preferably proximate the rear edge 32. Similarly, at least one elastic member 62b extends from a position in the mid portion 40 of the article 10 to a position in the rear portion 30 of the article 10, preferably proximate the rear edge 32. Preferably, the elastic members 62a, 62b follow the contour of the edge of the absorbent body 16. The elastic members 62a, 62b are preferably applied to the absorbent article 10 under tension, so that when the article is unfolded (e.g., when it is in use), tension in the elastic members 62a, 62b facilitates forming the rear portion 30 of the absorbent article 10 to the body of the wearer. The elastic members 62a, 62b thereby facilitate shaping the absorbent article 10 in a manner to reduce its conspicuousness and increase its comfort when in use.

The elastic members 62a, 62b are preferably applied to a surface of the inner sheet 14 that faces the absorbent body 16 according to known methods so that the elastic members 62a, 62b are disposed between the inner sheet 14 and the absorbent body 16.

The elastic members 60a and 62a are preferably formed from one continuous length of elastic material, and the elastic members 60b and 62b are formed from one continuous length of elastic material, as illustrated in FIG. 1. In another embodiment, each of the elastic members 60a, 62a and 60b, 62b are formed from a plurality of parallel continuous strands of elastic material. Preferably each of the strands are equal in size and strength and are applied with equal tension. The plurality of strands may include three strands.

The strands that define the elastic member 60a are secured to the fold 50a starting in the front portion 20, proximate front edge 22 and extend to a location in the mid portion 40 of the absorbent article 10. As can be seen in FIG. 2, the elastic members 60a, 60b are secured within the folds 50a, 50b. At the mid portion 40, the elastic strands defining the elastic members 60a, 60b are continuous with the elastic members 62a, 62b and transition from the folds 50a, 50b outwardly to follow the contour of the absorbent body 16 toward the rear portion of the absorbent article 10. In alternate embodiments of the invention, the respective elastic members may be formed discretely. The invention does not require the use of continuous strands.

The elastic members may be of any number of conventional constructions. The elastic members may comprise longitudinal elastic members, such as a cord-shaped or band-shaped core of an elastic material, for example rubber, with or without a wrapped-around thread cover that can be bonded with adhesives and enable the elastic to be anchored to the absorbent article. Alternately, a hot melt pressure sensitive elastomeric adhesive may be extruded onto the absorbent article. The elastic members may be attached to the article using known methods. For example, the elastic members 60a, 60b may be attached to the respective folds 50a, 50b using a technique described in U.S. Pat. No. 5,665,191 assigned to SCA Molnlycke AB, Gothenburg, Sweden, the disclosure of which is incorporated by reference here in its entirety. The elastic members 62a, 62b may be attached using conventional techniques.

Figure 3:
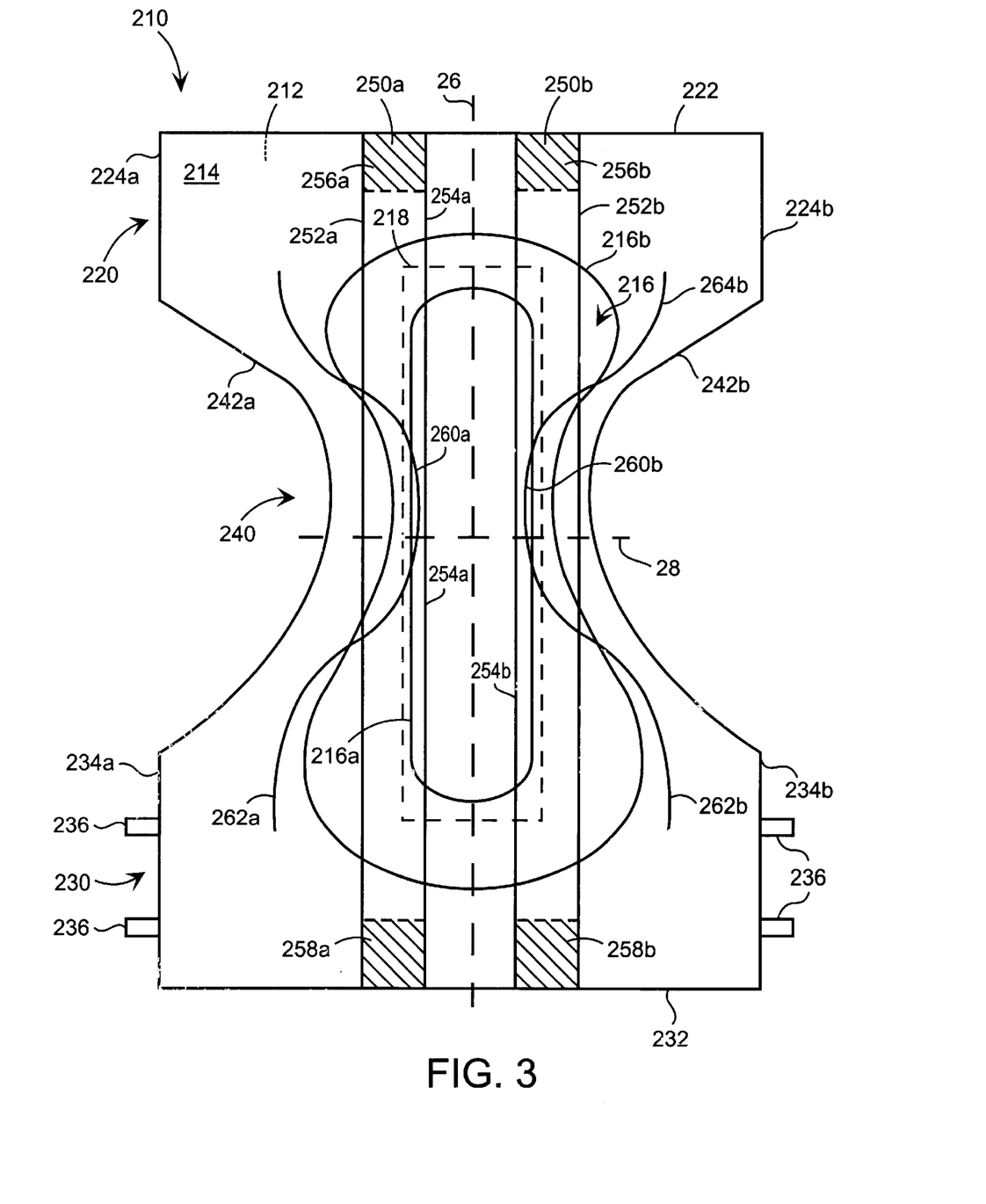
FIG. 3 is a plan view of an absorbent article in accordance with a second exemplary embodiment of the present invention.

FIG. 3 is a plan view illustrating a second embodiment of an absorbent article 210 that utilizes elastic members in the front portion 220 and the rear portion 230 to enhance the fit of article 210. The absorbent article 210 may be constructed in substantially the same manner as the absorbent article 10 of FIG. 1, and the description of common aspects of the construction of the article 210 will not be repeated.

Figure 4:
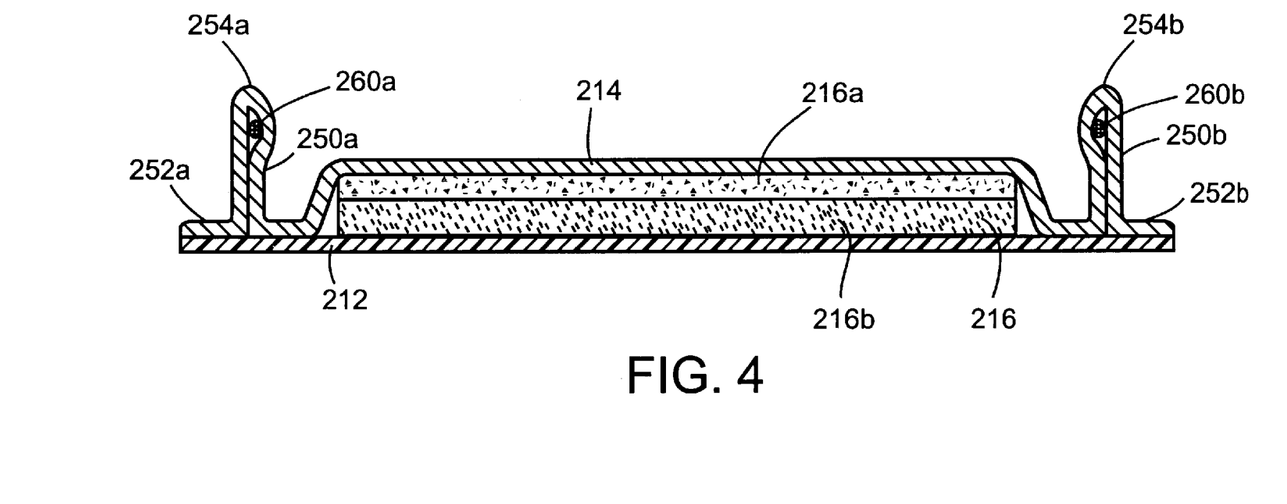
FIG. 4 is a cross-sectional view of the absorbent article depicted in FIG. 3 taken along line 28.

The cover sheet 212 may include a suitable material which typically is a substantially liquid impermeable material. Commonly used materials include a thin (e.g., 20μ) layer of polyethylene, polypropylene, polyvinyl-chloride, or other suitable material. The cover sheet 212 may be constructed of a single-layer or of multiple layers.

The absorbent body 216 may include materials suitable for absorbing bodily exudates. Known materials include cellulosic fibers, tissue, or super-absorbent materials, which are polymers capable of absorbing several times their own weight in liquids. The invention contemplates the use of multi-layered and/or composite absorbent bodies, which, by way of example, are described in U.S. Pat. No. 5,741,241 assigned to SCA Molnlycke AB, Gothenburg, Sweden. For example, the absorbent body 216 may include a first absorbent layer 216a that includes a cellulose fluff-pulp of large pore volume, high wet resiliency and low liquid-dispersion ability, and a second absorbent layer 216b comprised of cellulose fluff-pulp of low pore volume, low wet resiliency and high liquid-dispersion ability. Both absorbent layers may also include superabsorbent material. Or, either of the layers may include superabsorbent material.

The inner sheet 214 is attached to the inner surface of the cover sheet 212 with the absorbent body 216 secured between the cover sheet 212 and the inner sheet 214. The inner sheet 214 may be secured to the cover sheet 212 using conventional techniques, e.g., ultrasonic welding, adhesives, etc.

In a preferred embodiment, the inner sheet 214 is preferably a nonwoven material that is produced in a liquid impermeable condition so that it is substantially liquid impermeable under normal use conditions. The nonwoven material can be either hydrophilic or hydrophobic. The material is preferably an SMS material (spunbond-meltbond-spunbond). The permeability of the inner sheet is measured in mm of water according to a test called the Edana method No. 120.1-80.

A specific region of the inner sheet 214, referred to as a wetting area 218, may be treated, e.g., by exposure to a hydrophilic surfactant, to make the wetting area 218 liquid permeable. As such, the wetting area 218 preferably has a permeability of 0 mm $H_2O$, and the portions of the inner sheet forming the folds 250a, 250b preferably have a permeability of at least 20 mm $H_2O$.

Alternately, the inner sheet 214 may be formed from a liquid permeable material.

When laid flat, the absorbent article 210 has a substantially hour-glass contour and has a length extending along a major or longitudinal axis 6 and a width extending along a minor axis 8 perpendicular to longitudinal axis 6. A first longitudinal end constitutes a front portion 220 (also referred to as a front region), and the other end constitutes a rear portion 230 (also referred to as a rear region). A mid portion 240 (also referred to as a mid region) is located between the front portion 220 and the rear portion 230.

The front portion 220 includes a front edge 222 and side edges 224a and 224b. In the embodiment illustrated in FIG. 3, the front edge 222 is substantially straight; however, it will be appreciated that the front edge 222 may be contoured or curved to adapt to a desired shape in use. Similarly, the side edges 224a, 224b are depicted as substantially straight, but may be contoured or curved as desired.

The rear portion 230 includes a rear edge 232 and side edges 234a, 234b, which are depicted as straight but may be contoured or curved as desired. The rear portion 230 further includes fasteners 236. Tapes, hook and loop material, pins, and other conventional fasteners are all known fasteners in the incontinence garment art, and are only some of the types of fasteners which may be used with this embodiment. In use, the side edge 224a is fastened to the side edge 234a and the side edge 224b is fastened to side edge 234b to define a waist portion of a disposable absorbent garment.

The mid portion 240 includes contoured edges 242a, 242b. In use, the contoured edges 242a, 242b are adapted to be disposed adjacent the legs of the wearer of the absorbent article 210 proximate the crotch area, and the mid portion 240 is positioned to receive and retain bodily exudates.

The inner sheet 214 may be applied to the cover sheet 212 such that a first fold 250a and a second fold 250b are incorporated therein along the longitudinal length of the article at a location proximate each edge of the narrowest part of the absorbent body 216. This may be accomplished, for example, by forming suitable folds 250a, 250b in the inner sheet 214 before or while connecting the inner sheet 214 to the cover sheet 212. The folds 250a, 250b include proximal edges 252a and 252b in contact with the inner sheet 214 and distal edges 254a and 254b opposite the proximal edges 252a, 252b.

In the embodiment depicted in FIG. 3, the folds 250a, 250b extend from the front edge 222 to the rear edge 232 along axes substantially parallel to the longitudinal axis 6. It will be appreciated, however, that the folds 250a, 250b may follow a convex or concave arc from front the front section 220 to the rear section 230 of the absorbent article 210. The entire width of the fold 250a may be connected to the surface of the garment at a front portion 256a and at a rear portion 258a. Similarly, the entire width of the fold 250b may be connected to the surface of the garment at a front portion 256b and at a rear portion 258b. In the embodiment of the invention which utilizes a liquid impermeable inner sheet 214, the folds of the inner sheet 214 are made from the liquid impermeable portion of the inner sheet 214, such that the folds are substantially liquid impermeable.

Elastic members 260a, 260b extend along a portion of the length of the respective folds 250a, 250b in the mid portion 240 of the absorbent article 210. The elastic members 260a, 260b are preferably applied to the absorbent article 210 under tension, so that when the article is unfolded (e.g., when it is in use), tension in the elastic members 260a, 260b gathers the distal edges 254a, 254b of the folds 250a, 250b and urges them away from the surface of the inner sheet 214. The folds 250a, 250b thereby form barriers to inhibit the leakage of bodily exudates from the mid region 240 of the absorbent article 210. In the areas where the elastics gather the folds and urge the folds away from the surface of the inner sheet, the folds may be referred to as standing gathers.

As an alternative to applying the inner sheet 214 with the folds described in the preceding paragraph and illustrated in FIGS. 3 and 4, a substantially flat inner sheet 214 may be used, i.e., without the folds. In this case, separate sheets of material may be applied to the surface of the inner sheet 214 to form the folds. See, for example, the embodiments illustrated in FIGS. 5–8.

Elastic members 262a, 262b extend from the mid portion 240 of article 210 toward the rear portion 230 of article 210. Preferably, the elastic members 262a, 262b follow the contour of the edge of the absorbent body 216. The elastic members 262a, 262b are preferably applied to the absorbent article 210 under tension, so that when the article is unfolded (e.g., when it is in use), tension in the elastic members 262a, 262b facilitates forming the rear portion 230 of the absorbent article 210 to the body of the wearer. The elastic members 262a, 262b thereby facilitate shaping the absorbent article 210 in a manner to reduce its conspicuousness and increase its comfort when in use.

The elastic members 262a, 262b are preferably applied to a surface of the inner sheet 214 that faces the absorbent body 216 according to known methods so that the elastic members 262a, 262b are disposed between the inner sheet 214 and the absorbent body 216.

Elastic members 264a, 264b extend from the mid portion 240 of the article 210 toward the front portion 220 of the article 210. Preferably, the elastic members 264a, 264b follow the contour of the edge of the absorbent body 216. The elastic members 264a, 264b are preferably applied to the absorbent article 210 under tension, so that when the article is unfolded (e.g., when it is use), tension in the elastic members 264a, 264b facilitates forming the front portion 220 of the absorbent article 210 to the body of the wearer. The elastic members 264a, 264b thereby facilitate shaping the absorbent article 210 in a manner to reduce its conspicuousness and increase its comfort when in use.

The elastic members 264a, 264b are preferably applied to a surface of the inner sheet 214 that faces the absorbent body 216 according to known methods so that the elastic members 264a, 264b are disposed between the inner sheet 214 and the absorbent body 216.

In one embodiment, the elastic members 260a, 262a, and 264a are formed from a continuous strand of elastic material. The strand that defines the elastic member 264a is secured to the inner sheet 214 and follows the contour of the absorbent body 216 to the mid portion 240. At this location, the elastic strand transitions into the fold 250a to define the elastic member 260a that extends longitudinally along the fold 250a in the mid portion 240. At a location near the rear of the mid portion 240, the elastic strand transitions from the fold 250a to define the elastic member 262a, which follows the contour of the absorbent body 216 toward the rear portion 230 of the absorbent article 210. The elastic members 260b, 262b, 264b may also be formed from a continuous strand of elastic material. In alternate embodiments of the invention, the respective elastic members may be formed discretely. The invention does not require the use of continuous strands.

The elastic members may be of any number of conventional constructions. The elastic members may comprise longitudinal elastic members, such as a cord-shaped or band-shaped core of an elastic material, for example rubber, with or without a wrapped-around thread cover that can be bonded with adhesives and enable the elastic to be anchored to the absorbent article. Alternately, a hot melt pressure sensitive elastomeric adhesive may be extruded onto the absorbent article. The elastic members may be attached to the article using known methods. For example, the elastic members 260a, 260b may be attached to the respective folds 250a, 250b using a technique described in U.S. Pat. No. 5,665,191. The elastic members 262a, 262b may be attached using conventional techniques.

Figure 5:
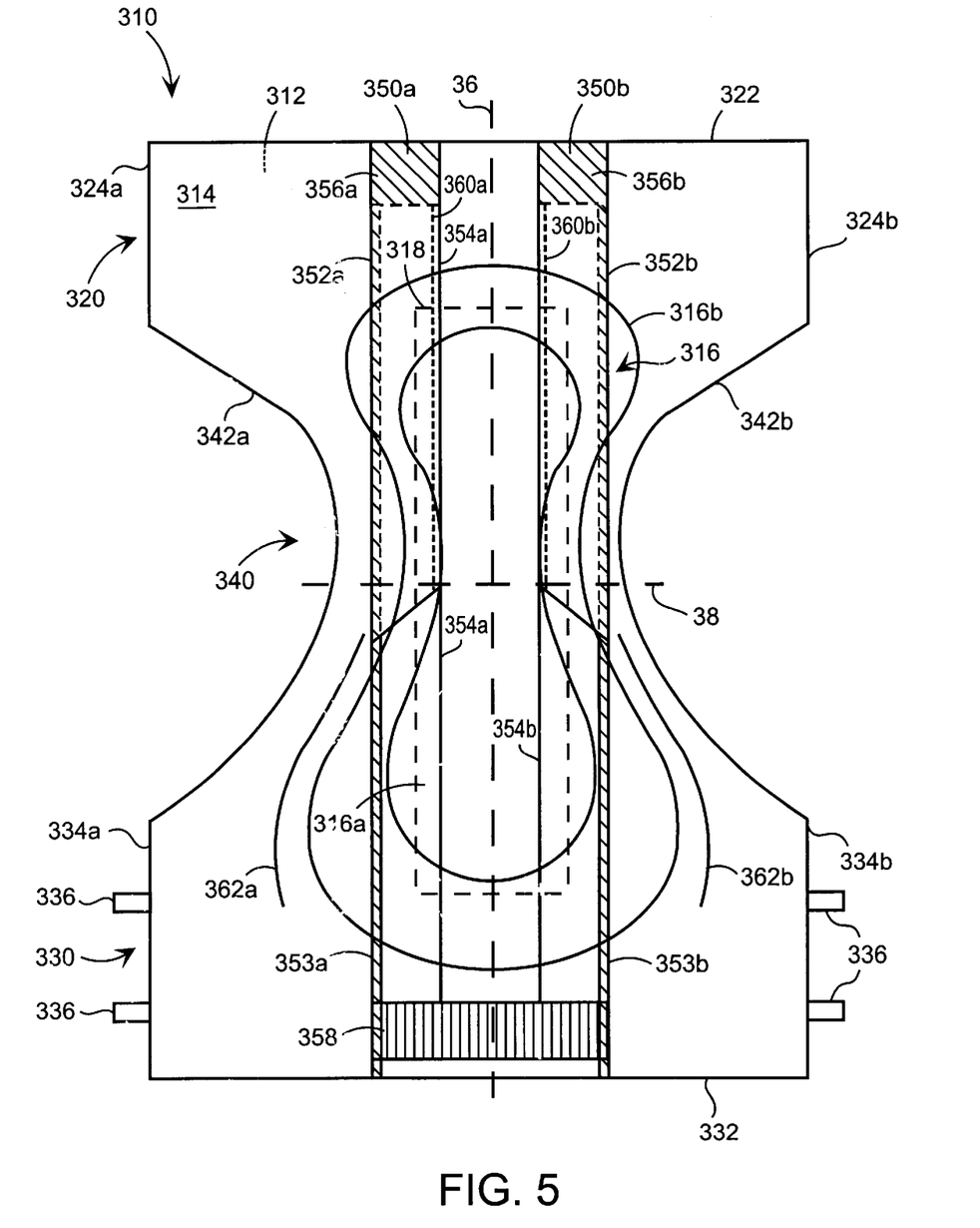
FIG. 5 is a plan view of an absorbent article in accordance with a third exemplary embodiment of the present invention.
Figure 6:
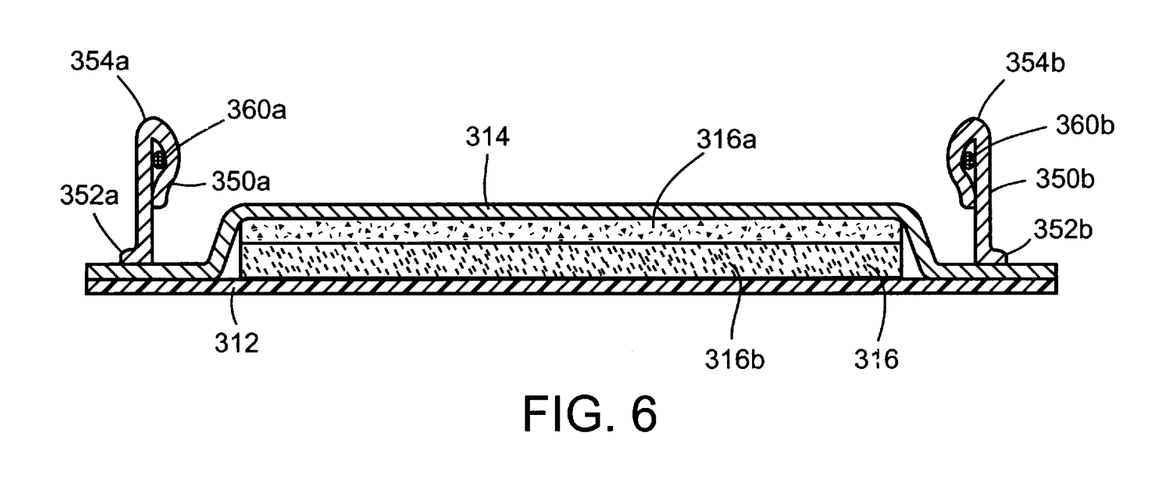
FIG. 6 is a cross-sectional view of the absorbent article depicted in FIG. 5 taken along line 38.

A third embodiment is illustrated in FIGS. 5–6, wherein an absorbent article 310 in accordance with the invention includes an inner sheet 314 intended to be positioned in contact with the body of a user, an absorbent body 316 for receiving and retaining bodily exudates (e.g., urine and fecal matter), and a cover sheet 312. A first strip 350a and a second strip 350b extend partially along the surface of inner sheet 314 parallel to a longitudinal axis 36 of the absorbent article 310. Strips 350a, 350b include respective elastics 360a, 360b extending along at least a portion of their length.

The strips 350a, 350b can be made from the same material as the inner sheet 314, but are separate pieces of material. The strips 350a, 350b are secured to the inner sheet 314 with a suitable adhesive along proximal edges 352a, 352b, respectively. At the distal edges 354a, 354b of the strips, the material is folded over the elastics 360a, 360b, as illustrated in FIG. 6.

The cover sheet 312 may include a suitable material which typically is a substantially liquid impermeable material. Commonly used materials include a thin (e.g., 20μ) layer of polyethylene, polypropylene, polyvinyl-chloride, or other suitable material. The cover sheet 312 may be constructed of a single-layer or of multiple layers.

The absorbent body 316 may include materials suitable for absorbing bodily exudates. Known materials include cellulosic fibers, tissue, or super-absorbent materials, which are polymers capable of absorbing several times their own weight in liquids. The invention contemplates the use of multi-layered and/or composite absorbent bodies, which, by way of example, are described in U.S. Pat. No. 5,741,241 assigned to SCA Molnlycke AB, Gothenburg, Sweden. For example, the absorbent body 316 may include a first absorbent layer 316a that includes a cellulose fluff-pulp of large pore volume, high wet resiliency and low liquid-dispersion ability, and a second absorbent layer 316b comprised of cellulose fluff-pulp of low pore volume, low wet resiliency and high liquid-dispersion ability. Both absorbent layers may also include superabsorbent material. Or, either of the layers may include superabsorbent material.

The inner sheet 314 is attached to the inner surface of the cover sheet 312 with the absorbent body 316 secured between the cover sheet 312 and the inner sheet 314. The inner sheet 314 may be secured to the cover sheet 312 using conventional techniques, e.g., ultrasonic welding, adhesives, etc.

In a preferred embodiment, the inner sheet 314 is preferably a nonwoven material that is produced in a liquid impermeable condition so that it is substantially liquid impermeable under normal use conditions. The nonwoven material can be either hydrophilic or hydrophobic. The material is preferably an SMS material (spunbond-meltbond-spunbond). The permeability of the inner sheet is measured in mm of water according to a test called the Edana method No. 120.1-80.

A specific region of the inner sheet 314, referred to as a wetting area 318, may be treated, e.g., by exposure to a hydrophilic surfactant, to make the wetting area 318 liquid permeable. As such, the wetting area 318 preferably has a permeability of 0 mm $H_2O$, and the strips 350a, 350b preferably have a permeability of at least 20 mm $H_2O$.

Alternately, the inner sheet 314 may be formed from a liquid permeable material.

FIG. 5 is a plan view of the third embodiment disposed in a substantially flat position. Referring to FIG. 5, when laid flat, the absorbent article 310 has a substantially hour-glass contour and has a length extending along a major or longitudinal axis 36 and a width extending along a minor axis 38 perpendicular to longitudinal axis 36. A first longitudinal end constitutes a front portion 320 (also referred to as a front region), and the other end constitutes a rear portion 330 (also referred to as a rear region). A mid portion 340 (also referred to as a mid region) is located between the front portion 320 and the rear portion 330.

The front portion 320 includes a front edge 322 and side edges 324a and 324b. The front edge 322 is substantially straight; however, it will be appreciated that the front edge 322 may be contoured or curved to adapt to a desired shape in use. Similarly, the side edges 324a, 324b are depicted as substantially straight, but may be contoured or curved as desired.

The rear portion 330 includes a rear edge 332 and side edges 334a, 334b, which are depicted as straight but may be contoured or curved as desired. The rear portion 330 further includes fasteners 336. Tapes, hook and loop material, pins, and other conventional fasteners are all known fasteners in the incontinence garment art, and are only some of the types of fasteners which may be used with this embodiment. In use, the side edge 324a is fastened to the side edge 334a and the side edge 324b is fastened to the side edge 334b to define a waist portion of a disposable absorbent garment.

The mid portion 340 includes contoured edges 342a, 342b. In use, the contoured edges 342a, 342b are adapted to be disposed adjacent the legs of the wearer of the absorbent article 310 proximate the crotch area, and the mid portion 340 is positioned to receive and retain bodily exudates.

In the embodiment depicted in FIGS. 5–6, the major part of the strips 350a, 350b extends from the front edge 322 to a portion about midway along the article 310. A narrow portion 353a, 353b of the strip may continue to the rear edge 332 along axes substantially parallel to the longitudinal axis 36. It will be appreciated, however, that the strips 350a, 350b may follow a convex or concave arc from front the front section 320 to the rear section 330 of the absorbent article 310. The strip 350a may be connected to the surface of the garment at a front portion 356a. Similarly, the strip 350b may be connected to the surface of the garment at a front portion 356b. In the embodiment of the invention which utilizes a liquid impermeable inner sheet 314, the strips 350a, 350b are preferably substantially liquid impermeable.

At least one elastic member 362a extends along a portion of the absorbent body 316 from near the rear end of the absorbent body 316 to a region near the center of the absorbent body 316. Similarly, at least one elastic member 362b extends along the other side of the absorbent body 316 from near the rear end of the absorbent body 316 to a region near the center of the absorbent body 316. The elastic members 362a, 362b are preferably applied to the absorbent article 310 under tension, so that when the article is unfolded (e.g., when it is in use), tension in the elastic members 362a, 362b helps gather the inner sheet 314 and the cover sheet 312 into gathers, shape the absorbent article 310, and increase its comfort.

Similarly, the elastics 360a, 360b extending along the distal edges of the strips 350a, 350b gather the distal edges 354a, 354b of the strips 350a, 350b and urges the distal edges 354a, 354b away from the surface of the inner sheet 314. The strips 350a, 350b thereby form barriers to inhibit the leakage of bodily exudates from the mid region 340 and front region 320 of the absorbent article 310. In the areas where the elastics gather the strips and urge the strips away from the surface of the inner sheet, the strips may be referred to as standing gathers.

The elastic members 362a, 362b are preferably applied to a surface of the inner sheet 314 that faces the absorbent body 316 according to known methods so that the elastic members 362a, 362b are disposed between the inner sheet 314 and the cover sheet 312.

In one embodiment of the invention, the elastic members 362a and 362b are each formed from one continuous length of elastic material. In another embodiment, each of the elastic members 362a and 362b are formed from a plurality of parallel continuous strands of elastic material. Preferably each of the strands are equal in size and strength and are applied with equal tension. The plurality of strands may include three strands.

As can be seen in FIG. 6, the elastic members 360a, 360b are secured within the folds of the strips 350a, 350b. The elastics 360a, 360b may be either a single elastic, or may constitute a plurality of parallel elastics.

The elastic members may be of any number of conventional constructions. The elastic members may comprise longitudinal elastic members, such as a cord-shaped or band-shaped core of an elastic material, for example rubber, with or without a wrapped-around thread cover that can be bonded with adhesives and enable the elastic to be anchored to the absorbent article. Alternately, a hot melt pressure sensitive elastomeric adhesive may be extruded onto the absorbent article. The elastic members may be attached to the article using known methods. For example, the elastic members 360a, 360b may be attached to the respective folds using a technique described in U.S. Pat. No. 5,665,191 assigned to SCA Molnlycke AB, Gothenburg, Sweden.

The absorbent article further includes an elasticized strip 358 extending along the rear portion 330 of the article 310. The elasticized strip 358 tends to gather the rear portion 330 widthwise using elastication in an expandable manner to provide a certain amount of possible expansion of the article during movement.

Figure 7:
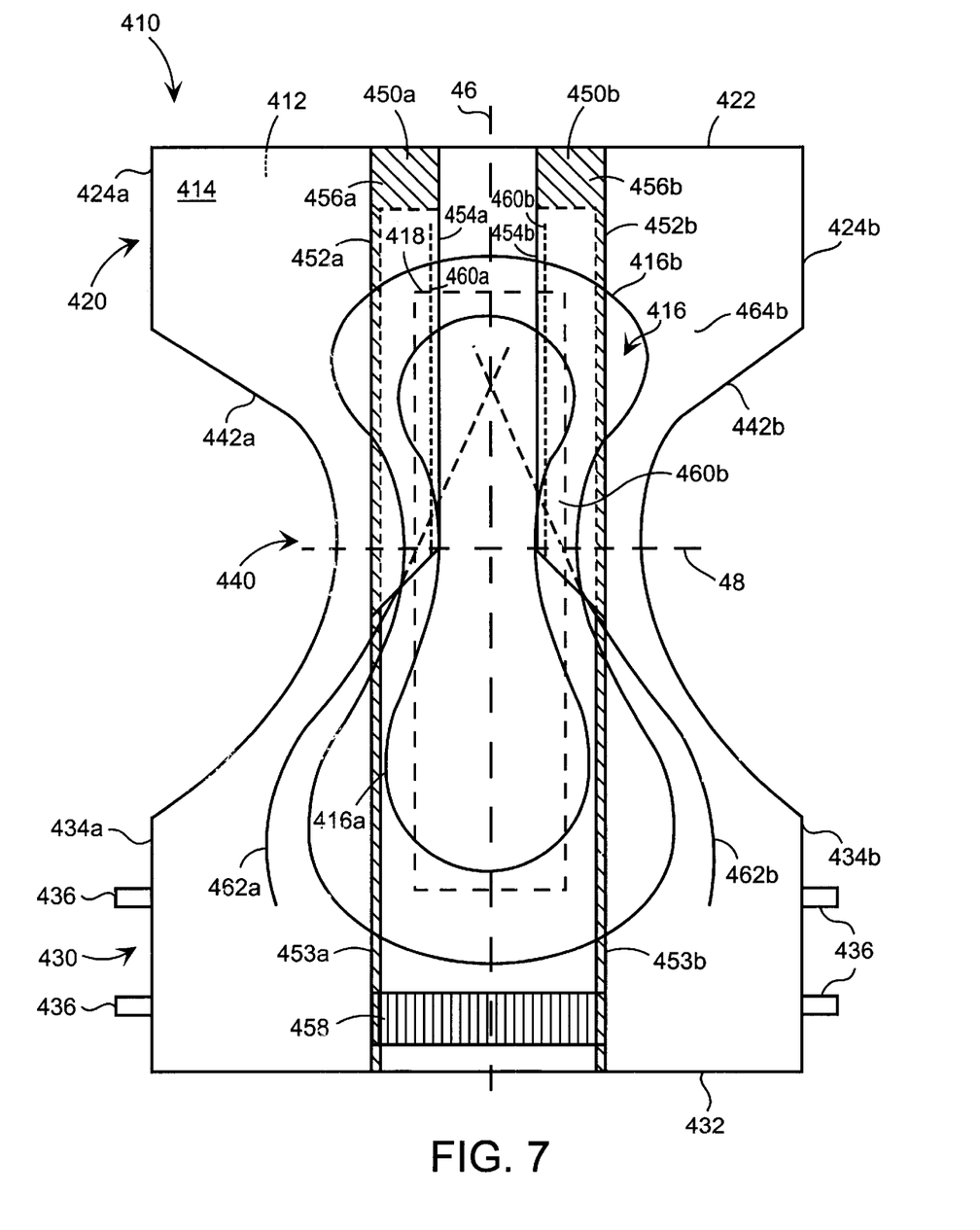
FIG. 7 is a plan view of an absorbent article in accordance with a fourth exemplary embodiment of the present invention.
Figure 8:
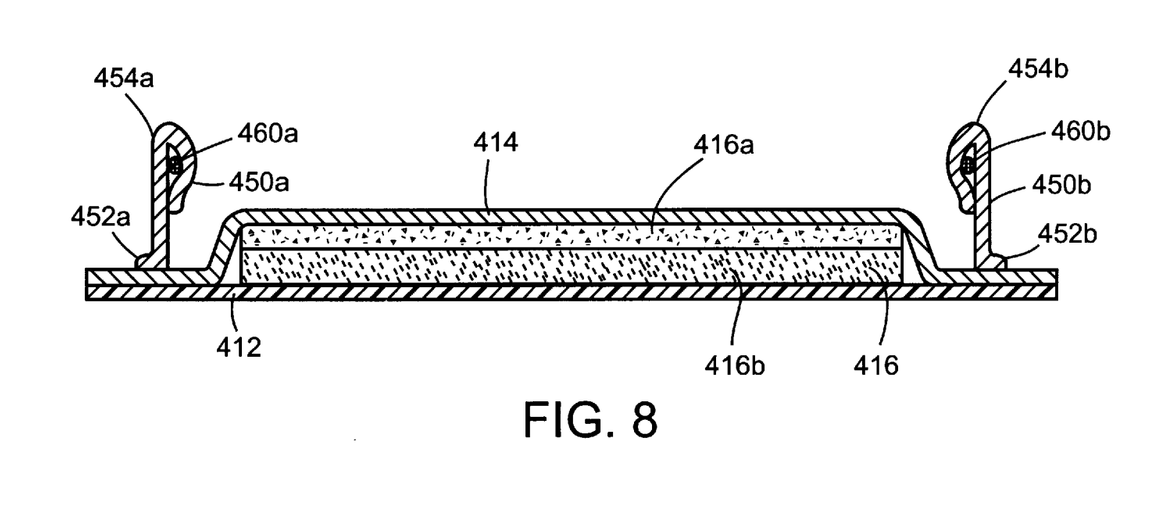
FIG. 8 is a cross-sectional view of the absorbent article depicted in FIG. 7 taken along line 48.

FIGS. 7 and 8 illustrate a fourth embodiment of an absorbent article 410 that is similar to the third embodiment 310. The absorbent article 410 in accordance with the invention includes an inner sheet 414 intended to be positioned in contact with the body of a user, an absorbent body 416 for receiving and retaining bodily exudates (e.g., urine and fecal matter), and a cover sheet 412. A first strip 450a and a second strip 450b extend partially along the surface of inner sheet 414 parallel to a longitudinal axis 46 of the absorbent article 410. Strips 450a, 450b include respective elastics 460a, 460b extending along at least a portion of their length.

The strips 450a, 450b can be made from the same type of material as the inner sheet 414, but are preferably separate pieces of material. The strips 450a, 450b are secured to the inner sheet 414 with a suitable adhesive along proximal edges 452a, 452b, respectively. At the distal edges 454a, 454b of the strips, the material is folded over the elastics 460a, 460b, as illustrated in FIG. 8.

The cover sheet 412 may include a suitable material which typically is a substantially liquid impermeable material. Commonly used materials include a thin (e.g., $20\mu$) layer of polyethylene, polypropylene, polyvinyl-chloride, or other suitable material. The cover sheet 412 may be constructed of a single-layer or of multiple layers.

The absorbent body 416 may include materials suitable for absorbing bodily exudates. Known materials include cellulosic fibers, tissue, or super-absorbent materials, which are polymers capable of absorbing several times their own weight in liquids. The invention contemplates the use of multi-layered and/or composite absorbent bodies, which, by way of example, are described in U.S. Pat. No. 5,741,241 assigned to SCA Molnlycke AB, Gothenburg, Sweden. For example, the absorbent body 416 may include a first absorbent layer 416a that includes a cellulose fluff-pulp of large pore volume, high wet resiliency and low liquid-dispersion ability, and a second absorbent layer 416b comprised of cellulose fluff-pulp of low pore volume, low wet resiliency and high liquid-dispersion ability. Both absorbent layers may also include superabsorbent material. Or, either of the layers may include superabsorbent material.

The inner sheet 414 is attached to the inner surface of the cover sheet 412 with the absorbent body 416 secured between the cover sheet 412 and the inner sheet 414. The inner sheet 414 may be secured to the cover sheet 412 using conventional techniques, e.g., ultrasonic welding, adhesives, etc.

In a preferred embodiment, the inner sheet 414 is preferably a nonwoven material that is produced in a liquid impermeable condition so that it is substantially liquid impermeable under normal use conditions. The nonwoven material can be either hydrophilic or hydrophobic. The material is preferably an SMS material (spunbond-meltbond-spunbond). The permeability of the inner sheet is measured in mm of water according to a test called the Edana method No. 120.1-80.

A specific region of the inner sheet 414, referred to as a wetting area 418, may be treated, e.g., by exposure to a hydrophilic surfactant, to make the wetting area 418 liquid permeable. As such, the wetting area 418 preferably has a permeability of 0 mm $H_2O$, and the strips 450a, 450b preferably have a permeability of at least 20 mm $H_2O$.

Alternately, the inner sheet 414 may be formed from a liquid permeable material.

Referring to FIG. 7, when laid flat, the absorbent article 410 has a substantially hour-glass contour and has a length extending along a major or longitudinal axis 46 and a width extending along a minor axis 48 perpendicular to longitudinal axis 46. A first longitudinal end constitutes a front portion 420 (also referred to as a front region), and the other end constitutes a rear portion 430 (also referred to as a rear region). A mid portion 440 (also referred to as a mid region) is located between the front portion 420 and the rear portion 430.

The front portion 420 includes a front edge 422 and side edges 424a and 424b. The front edge 422 is substantially straight; however, it will be appreciated that the front edge 422 may be contoured or curved to adapt to a desired shape in use. Similarly, the side edges 424a, 424b are depicted as substantially straight, but may be contoured or curved as desired.

The rear portion 430 includes a rear edge 432 and side edges 434a, 434b, which are depicted as straight but may be contoured or curved as desired. The rear portion 430 further includes fasteners 436. Tapes, hook and loop material, pins, and other conventional fasteners are all known fasteners in the incontinence garment art, and are only some of the types of fasteners which may be used with this embodiment. In use, the side edge 424a is fastened to the side edge 434a and the side edge 424b is fastened to the side edge 434b to define a waist portion of a disposable absorbent garment.

The mid portion 440 includes contoured edges 442a, 442b. In use, the contoured edges 442a, 442b are adapted to be disposed adjacent the legs of the wearer of the absorbent article 410 proximate the crotch area, and the mid portion 440 is positioned to receive and retain bodily exudates.

In the embodiment depicted in FIGS. 7–8, the major part of the strips 450a, 450b extends from the front edge 422 to a portion about midway along the article 410. A narrow portion 453a, 453b of the strip may continue to the rear edge 432 along axes substantially parallel to the longitudinal axis 46. It will be appreciated, however, that the strips 450a, 450b may follow a convex or concave arc from front the front section 420 to the rear section 430 of the absorbent article 410. The strip 450a may be connected to the surface of the garment at a front portion 456a. Similarly, the strip 450b may be connected to the surface of the garment at a front portion 456b. In the embodiment of the invention which utilizes a liquid impermeable inner sheet 414, the strips 450a, 450b are preferably substantially liquid impermeable.

At least one elastic member 462a extends along a portion of the absorbent body 416 from near the rear end 430 of the absorbent body 416 to a region between the midsection and the front portion 420. Similarly, at least one elastic member 462b extends along the other side of the absorbent body 416 from near the rear end 430 of the absorbent body 416 to a region between the midsection and the front portion 420. The elastic members 462a, 462b are preferably applied to the absorbent article 410 under tension, so that when the article is unfolded (e.g., when it is use), tension in the elastic members 462a, 462b help gather the inner sheet 414 and the cover sheet 412 into gathers, shape the absorbent article 410, and increase its comfort. In the areas where the elastics gather the strips and urge the strips away from the surface of the inner sheet, the strips may be referred to as standing gathers.

Similarly, elastics 460a, 460b extending along the distal edges of the strips 450a, 450b gather the distal edges 454a, 454b of the strips 450a, 450b and urge the distal edges 454a, 454b away from the surface of the inner sheet 414. The strips 450a, 450b thereby form barriers to inhibit the leakage of bodily exudates from the mid region 440 of the absorbent article 410.

The elastic members 462a, 462b are preferably applied to a surface of the cover sheet 412 that faces the absorbent body 416 according to known methods so that the elastic members 462a, 462b are disposed between the inner sheet 414 and the cover sheet 412 at the rear end thereof. As the elastics 462a, 462b approach the center section 440, they pass underneath the absorbent body 416 so that they are secured between the absorbent body 416 and the cover sheet 412. At the front end of the article 410, the elastics 462a, 462b intersect and cross over each other.

In one embodiment of the invention, the elastic members 462a and 462b are each formed from one continuous length of elastic material. In another embodiment, each of the elastic members 462a and 462b are formed from a plurality of parallel continuous strands of elastic material. Preferably each of the strands are equal in size and strength and are applied with equal tension. The plurality of strands may include three strands.

As can be seen in FIG. 8, the elastic members 460a, 460b are secured within the folds of the strips 450a, 450b. The elastics 460a, 460b may be either a single elastic, or may constitute a plurality of parallel elastics.

The elastic members may be of any number of conventional constructions. The elastic members may comprise longitudinal elastic members, such as a cord-shaped or band-shaped core of an elastic material, for example rubber, with or without a wrapped-around thread cover that can be bonded with adhesives and enable the elastic to be anchored to the absorbent article. Alternately, a hot melt pressure sensitive elastomeric adhesive may be extruded onto the absorbent article. The elastic members may be attached to the article using known methods. For example, the elastic members 460a, 460b may be attached to the respective folds using a technique described in U.S. Pat. No. 5,665,191 assigned to SCA Molnlycke AB, Gothenburg, Sweden.

The absorbent article further includes an elasticized strip 458 extending along the rear portion 430 of the article 410. The elasticized strip 458 tends to gather the rear portion 430 widthwise using elastication in an expandable manner to provide a certain amount of possible expansion of the article during movement.

In each of the embodiments disclosed herein, it is preferable that the elastics arranged between the cover sheet and the inner sheet gather a portion of the inner and outer sheets. It is also preferable that the elasticized or gathered sections of the folds or strips extending from the inner sheet do not materially overlap with the gathered portions of the inner and outer sheets. However, in some embodiments of the present invention, not specifically described herein, overlap of the gathered sections is possible.

The various embodiments of the present invention have been disclosed as using either folds within the inner sheet to form the standing gathers or as using separate strips of material secured to the inner sheet to form the standing gathers. In most cases, the embodiments disclosed with folds may be modified so that the standing gathers can be made from strips, and the embodiments disclosed with strips may be modified so that the standing gathers can be made from folds. In either case, the folds or strips may also be referred to generically as barriers.

The present invention has been described with reference to particular exemplary embodiments. However, it will be appreciated that the invention is not limited to the illustrated exemplifying embodiments and that numerous modifications can be made within the scope of the following claims.

What is claimed is:

1. A disposable, liquid absorbent article having a front portion, a rear portion, and a mid portion between the front portion and the rear portion, the article comprising:
   a liquid impervious cover sheet;
   an inner sheet connected to the cover sheet;
   an absorbent body disposed between the inner sheet and the cover sheet and having a major axis extending substantially along a longitudinal axis of the article;
   a first barrier extending from the inner sheet on a first side of the longitudinal axis substantially along an axis parallel to the longitudinal axis, the first barrier extending from at least the front portion and the mid portion of the article, the first barrier having elastication extending only from a first longitudinal position to a second longitudinal position, wherein the first longitudinal position is at the front portion and the second longitudinal position is at the mid portion;
   a second barrier extending from the inner sheet on a second side of the longitudinal axis substantially along an axis parallel to the longitudinal axis, the second barrier extending from at least the front portion and the mid portion of the article, the second barrier having elastication extending only from the first longitudinal position to the second longitudinal position;
   a first elasticizing means fastened to at least one of the inner sheet and the cover sheet on the first side of the longitudinal axis and extending along an outer edge of the absorbent article from only about the second longitudinal position to a third longitudinal position, wherein the third longitudinal position is at the rear portion, so as to gather a portion of the inner sheet and the cover sheet; and
   a second elasticizing means fastened to at least one of the inner sheet and the cover sheet on the second side of the longitudinal axis and extending along an outer edge of the absorbent article from only about the second longitudinal position to the third longitudinal position, so as to gather a portion of the inner sheet and the cover sheet.

2. The disposable, liquid absorbent article according to claim 1, wherein the inner sheet is formed from a substantially liquid impermeable material and includes a wetting area treated such that the wetting area is liquid permeable.

3. The disposable, liquid absorbent article according to claim 1, wherein the inner sheet is formed from a nonwoven material treated with a hydrophobic surfactant to render a portion of the material liquid impermeable.

4. The disposable, liquid absorbent article according to claim 1, wherein the first and second barriers also extend from the rear portion of the absorbent article.

5. The disposable, liquid absorbent article according to claim 1, wherein the first and second barriers are liquid impermeable.

6. A disposable, liquid absorbent article having a front portion, a rear portion, and a mid portion between the front portion and the rear portion, the article comprising:
   a liquid impervious cover sheet;
   an inner sheet connected to the cover sheet;
   an absorbent body disposed between the inner sheet and the cover sheet and having a major axis extending substantially along a longitudinal axis of the article;
   a first barrier extending on a first side of the longitudinal axis substantially along an axis parallel to the longitudinal axis;
   a second barrier extending on a second side of the longitudinal axis substantially along an axis parallel to the longitudinal axis;
   a first elasticizing means extending along the first barrier only from a first longitudinal position to a second longitudinal position, wherein the second longitudinal position is in the mid portion of the article so as to gather at least a part of the first barrier, the first elasticizing means including a portion extending between the inner sheet and the cover sheet from about the second longitudinal position to a third longitudinal position in the rear portion of the article to gather a part of the inner sheet and the cover sheet which follows a contour adjacent a first edge of the absorbent body, wherein no gathered part of the first barrier overlaps along the longitudinal axis with any gathered part of the inner sheet and the cover sheet; and
   a second elasticizing means extending along the second barrier only from the first longitudinal position to the second longitudinal position, so as to gather at least a part of the second barrier, the second elasticizing means including a portion extending between the inner sheet and the cover sheet from about the second longitudinal position to the third longitudinal position in the rear portion of the article to gather a part of the inner sheet and the cover sheet which follows a contour adjacent a second edge of the absorbent body, wherein no gathered part of the second barrier overlaps along the longitudinal axis with any gathered part of the inner sheet and the cover sheet.

7. The disposable, liquid absorbent article according to claim 6, wherein the first longitudinal position is in the front portion of the article.

8. The disposable, liquid absorbent article according to claim 6, wherein the first longitudinal position is in the mid portion of the article.

9. The disposable, liquid absorbent article according to claim 8, wherein the first and second elasticizing means each extends from the first longitudinal position to the front portion of the article between the inner sheet and the cover sheet, following a contour adjacent the edges of the absorbent body.

10. The disposable, liquid absorbent article according to claim 6, wherein the inner sheet is formed from a substantially liquid impermeable material and includes a wetting area treated such that the wetting area is liquid permeable.

11. The disposable, liquid absorbent article according to claim 6, wherein the inner sheet is formed from a nonwoven material treated with a hydrophobic surfactant to render a portion of the material liquid impermeable.

12. The disposable, liquid absorbent article according to claim 11, wherein the first and second barriers are formed from a nonwoven material treated with a hydrophobic surfactant to render the material liquid impermeable.

13. The disposable, liquid absorbent article according to claim 6, wherein the first and second barriers and the inner sheet are formed from the same nonwoven material.

14. The disposable, liquid absorbent article according to claim 6, wherein the absorbent body comprises a first absorbent member and a second absorbent member.

15. The disposable, liquid absorbent article according to claim 6, wherein the cover sheet and the inner sheet define an hourglass contour when the article is opened in a substantially flat position.

16. A disposable, liquid absorbent article according to claim 6, further comprising a fastener for fastening the absorbent article to the body of a user.

17. The disposable, liquid absorbent article according to claim 6, wherein the elasticizing means are applied to the article such that the elasticizing means are under tension when the article is in use.

18. A disposable, liquid absorbent article having a front portion, a rear portion, and a mid portion between the front portion and a rear portion, the article comprising:
a liquid impervious cover sheet;
an inner sheet connected to the cover sheet;
an absorbent body disposed between the inner sheet and the cover sheet and having a major axis extending substantially along a longitudinal axis of the article;
a first barrier extending from the inner sheet on a first side of the longitudinal axis substantially along an axis parallel to the longitudinal axis, the first barrier extending from at least the front portion and the mid portion of the article, the first barrier having elastication extending only from a first longitudinal position to a second longitudinal position, wherein the first longitudinal position is at the front portion and the second longitudinal position is at the mid portion;
a second barrier extending from the inner sheet on a second side of the longitudinal axis substantially along an axis parallel to the longitudinal axis, the second barrier extending from at least the front portion and the mid portion of the article, the second barrier having elastication only from the first longitudinal position to the second longitudinal position;
a first elastic fastened to at least one of the inner sheet and the cover sheet on the first side of the longitudinal axis and extending along an outer edge of the absorbent article from only about the second longitudinal position to a third longitudinal position, wherein the third longitudinal position is at the rear portion, so as to gather a portion of the inner sheet and the cover sheet; and
a second elastic fastened to at least one of the inner sheet and the cover sheet on the second side of the longitudinal axis and extending along an outer edge of the absorbent article from only about the second longitudinal position to the third longitudinal position, so as to gather a portion of the inner sheet and the cover sheet.

19. The disposable, liquid absorbent article according to claim 18, wherein the inner sheet is formed from a substantially liquid impermeable material and includes a wetting area treated such that the wetting area is liquid permeable.

20. The disposable, liquid absorbent article according to claim 18, wherein the inner sheet is formed from a nonwoven material treated with a hydrophobic surfactant to render a portion of the material liquid impermeable.

21. The disposable, liquid absorbent article according to claim 18, wherein the first and second barriers also extend from the rear portion of the absorbent article.

22. The disposable, liquid absorbent article according to claim 18, wherein the first and second barriers are liquid impermeable.

23. A disposable, liquid absorbent article having a front portion, a rear portion, and a mid portion between the front portion and the rear portion, the article comprising:
a liquid impervious cover sheet;
an inner sheet connected to the cover sheet;
an absorbent body disposed between the inner sheet and the cover sheet and having a major axis extending substantially along a longitudinal axis of the article;
a first barrier extending on a first side of the longitudinal axis substantially along an axis parallel to the longitudinal axis;
a second barrier extending on a second side of the longitudinal axis substantially along an axis parallel to the longitudinal axis;
a first elastic extending along the first barrier only from a first longitudinal position to a second longitudinal position, wherein the second longitudinal position is in the mid portion of the article so as to gather at least a part of the first barrier, the first elastic including a portion extending between the inner sheet and the cover sheet from about the second longitudinal position to a third longitudinal position in the rear portion of the article to gather a part of the inner sheet and the cover sheet which follows a contour adjacent a first edge of the absorbent body, wherein no gathered part of the first barrier overlaps along the longitudinal axis with any gathered part of the inner sheet and the cover sheet; and
a second elastic extending along the second barrier only from the first longitudinal position to the second longitudinal position, so as to gather at least a part of the second barrier, the second elastic including a portion extending between the inner sheet and the cover sheet from about the second longitudinal position to the third longitudinal position in the rear portion of the article to gather a part of the inner sheet and the cover sheet which follows a contour adjacent a second edge of the absorbent body, wherein no gathered part of the second barrier overlaps along the longitudinal axis with any gathered part of the inner sheet and the cover sheet.

24. The disposable, liquid absorbent article according to claim 23, wherein the first longitudinal position is in the front portion of the article.

25. The disposable, liquid absorbent article according to claim 23, wherein the first longitudinal position is in the mid portion of the article.

26. The disposable, liquid absorbent article according to claim 25, wherein the first and second elastics each extends from the first longitudinal position to the front portion of the article between the inner sheet and the cover sheet, following a contour adjacent the edges of the absorbent body.

27. The disposable, liquid absorbent article according to claim 23, wherein the inner sheet is formed from a substantially liquid impermeable material and includes a wetting area treated such that the wetting area is liquid permeable.

28. The disposable, liquid absorbent article according to claim 23, wherein the elastics are applied to the article such that the elastics are under tension when the article is in use.

29. A disposable, liquid absorbent article having a front portion, a rear portion, and a mid portion between the front portion and the rear portion, the article comprising:
- a liquid impervious cover sheet;
- an inner sheet connected to the cover sheet;
- an absorbent body disposed between the inner sheet and the cover sheet and having a major axis extending substantially along a longitudinal axis of the article;
- a first barrier extending from the inner sheet on a first side of the longitudinal axis substantially along an axis parallel to the longitudinal axis, the first barrier extending from at least the front portion and the mid portion of the article, the first barrier having elastication extending only from a first longitudinal position to a second longitudinal position, wherein the first longitudinal position is at the front portion and the second longitudinal position is at the mid portion;
- a second barrier extending from the inner sheet on a second side of the longitudinal axis substantially along an axis parallel to the longitudinal axis, the second barrier extending from at least the front portion and the mid portion of the article, the second barrier having elastication extending from the first longitudinal position to the second longitudinal position;
- a first elastic fastened to at least one of the inner sheet and the cover sheet on the first side of the longitudinal axis and extending along an outer edge of the absorbent article from about the second longitudinal position to a third longitudinal position, wherein the third longitudinal position is at the rear position, so as to gather a portion of the inner sheet and the cover sheet, and wherein no gathered part of the first barrier overlaps along the longitudinal axis with any gathered part of the inner sheet and the cover sheet in the rear portion of the article; and
- a second elastic fastened to at least one of the inner sheet and the cover sheet on the second side of the longitudinal axis and extending along an outer edge of the absorbent article from about the second longitudinal position to the third longitudinal position, so as to gather a portion of the inner sheet and the cover sheet, and wherein no gathered part of the second barrier overlaps along the longitudinal axis with any gathered part of the inner sheet and the cover sheet in the rear portion of the article.

30. A disposable, liquid absorbent article having a front portion, a rear portion, and a mid portion between the front portion and the rear portion, the article comprising:
- a liquid impervious cover sheet;
- an inner sheet connected to the cover sheet;
- an absorbent body disposed between the inner sheet and the cover sheet and having a major axis extending substantially along a longitudinal axis of the article;
- a first barrier extending on a first side of the longitudinal axis substantially along an axis parallel to the longitudinal axis;
- a second barrier extending on a second side of the longitudinal axis substantially along an axis parallel to the longitudinal axis;
- a first elastic has a first segment extending along the first barrier only from a first longitudinal position to a second longitudinal position, wherein the second longitudinal position is in the mid portion of the article so as to gather at least a part of the first barrier, the first elastic including a second segment attached to either the inner sheet or the cover sheet and extending from about the second longitudinal position to a third longitudinal position in the rear portion of the article to gather a part of the inner sheet and the cover sheet which follows a contour adjacent a first edge of the absorbent body, wherein no gathered part of the first barrier overlaps along the longitudinal axis with any gathered part of the inner sheet and the cover sheet at the rear portion; and
- a second elastic has a first segment extending along the second barrier only from the first longitudinal position to the second longitudinal position, so as to gather at least a part of the second barrier, the second elastic including a second segment attached to either the inner sheet or the cover sheet and extending from about the second longitudinal position to a third longitudinal position in the rear portion of the article to gather a part of the inner sheet and the cover sheet which follows a contour adjacent a second edge of the absorbent body, wherein no gathered part of the second barrier overlaps along the longitudinal axis with any gathered part of the inner sheet and the cover sheet at the rear portion;
- wherein the first and second segments of the first elastic comprise one continuous strand or are comprised of at least two separate lengths and the first and second segments of the second elastic comprise one continuous strand or are comprised of at least two separate lengths.

31. The disposable, liquid absorbent article according to claim 30, wherein the first longitudinal position is in the front portion of the article.

32. The disposable, liquid absorbent article according to claim 30, wherein the first longitudinal position is in the mid portion of the article.

33. The disposable, liquid absorbent article according to claim 30, wherein the first and second elastics each extends from the first longitudinal position to the front portion of the article between the inner sheet and the cover sheet, following a contour adjacent the edges of the absorbent body.

34. The disposable, liquid absorbent article according to claim 30, wherein the elastics are applied to the article such that the elastics are under tension when the article is in use.

35. The disposable, liquid absorbent article according to claim 30, wherein no gathered part of the first barrier overlaps along the longitudinal axis with any gathered part of the inner sheet and the cover sheet, and no gathered part of the second barrier overlaps along the longitudinal axis with any gathered part of the inner sheet and the cover sheet.

* * * * *